United States Patent

Dockner et al.

Patent Number: 5,637,760
Date of Patent: Jun. 10, 1997

[54] PREPARATION OF 1,4-BUTANEDIOL MONO (METH)ACRYLATE BY ESTERIFICATION OF (METH)ACRYLIC ACID WITH 1,4-BUTANEDIOL, IN WHICH AN AQUEOUS SOLUTION OF UNCONVERTED 1,4-BUTANEDIOL IS OBTAINED

[75] Inventors: Toni Dockner, Meckenheim; Helmut Lermer, Ludwigshafen; Klaus Bittins, Frankenthal; Gerhard Nestler, Ludwigshafen; Gundo Brauch, Hassloch, all of Germany

[73] Assignee: BASF Aktiengesellschaft, Ludwigshafen, Germany

[21] Appl. No.: 541,414

[22] Filed: Oct. 10, 1995

[30] Foreign Application Priority Data

Oct. 11, 1994 [DE] Germany .......................... 44 36 241.2

[51] Int. Cl.$^6$ .................................................. C07C 67/48
[52] U.S. Cl. ................................................. 560/218
[58] Field of Search .................................. 514/218

[56] References Cited

FOREIGN PATENT DOCUMENTS

| 0465853 | 1/1992 | European Pat. Off. . |
| 848945 | 9/1952 | Germany . |
| 1043342 | 6/1959 | Germany . |
| 1518572 | 1/1969 | Germany . |
| 4228397 | 3/1994 | Germany . |

OTHER PUBLICATIONS

Lehrbuch der organischen Chemie, C.R. Noller, Springer Verlag, Heidelberg, 1960, pp. 639–692.

Primary Examiner—Paul J. Killos
Attorney, Agent, or Firm—Oblon, Spivak, McClelland, Maier & Neustadt, P.C.

[57] ABSTRACT

1,4-butanediol mono(meth)acrylate is prepared by esterification of (meth)acrylic acid with 1,4-butanediol, by a process in which an aqueous solution of unconverted 1,4-butanediol is obtained, wherein the 1,4-butanediol present in the aqueous solution is converted into readily volatile tetrahydrofuran in the presence of a catalytic amount of a strong acid and the tetrahydrofuran is separated off from the aqueous solution.

7 Claims, No Drawings

PREPARATION OF 1,4-BUTANEDIOL MONO (METH)ACRYLATE BY ESTERIFICATION OF (METH)ACRYLIC ACID WITH 1,4-BUTANEDIOL, IN WHICH AN AQUEOUS SOLUTION OF UNCONVERTED 1,4-BUTANEDIOL IS OBTAINED

The present invention relates to a process for the preparation of 1,4-butanediol mono(meth)acrylate by esterification of (meth)acrylic acid with 1,4-butanediol, in which an aqueous solution of unconverted 1,4-butanediol is obtained.

(Meth)acrylic acid is used as an abbreviation for acrylic acid or methacrylic acid.

1,4-Butanediol mono(meth)acrylate is known (cf. for example Ullmanns Enzyklopädie der technischen Chemie, Polyacryl-Verbin-dungen bis Quecksilber, Vol. 19, 4th Edition, Verlag Chemie (1980), page 10). Owing to their bifunctionality (hydroxyl group and monoethylenically unsaturated group), they are interesting starting compounds. For example, they are suitable as vinylically unsaturated comonomers in polymers which are produced by free radical polymerization and are suitable, for example, as binders. However, as alcoholic compounds they are also suitable, for example, for polymer-analogous reactions (for example condensation or addition reactions).

It is generally known that 1,4-butanediol monoacrylate can be prepared by direct esterification of (meth)acrylic acid with 1,4-butanediol in the presence of acidic esterification catalysts, with removal of the resulting water by azeotropic distillation with a suitable entraining agent.

The monoesters are formed in high yields essentially only when a large excess of the dihydric alcohol is used, since otherwise considerable amounts of diester are formed. To make such a process economical, it is necessary to recover this excess.

The fact that the alkanediol, monoester and diester have high boiling points even under reduced pressure, the boiling points of alkanediol, monoester and diester are very close together and the vinylically unsaturated monoesters and diesters have a high tendency to polymerize, especially in the condensed phase and at elevated temperatures is disadvantageous for such a separation task.

In the case of acrylic acid as starting acid, the relevant boiling points at atmospheric pressure (1 atm) are, for example:

1,4-butanediol: 230° C. (Römpp Chemie Lexikon, 9th Edition, Thieme Verlag, Stuttgart, 1989);

1,4-butanediol monoacrylate: about 230° C. (Technische Information M/ED 1331 d of BASF Aktiengesellschaft from 1987);

1,4-butanediol diacrylate: about 225° C. (Ullmanns Enzyklopädie der technischen Chemie, Vol. 19, Verlag Chemie, Weinheim, 1980, page 9).

Under such conditions, separation by rectification is unsatisfactory for economic reasons, this also being confirmed on page 1, lines 35 to 40, of DE-A 42 28 397.

German Patent 1,518,572 and EP-A 465 853 therefore relate to processes for the preparation of 1,4-butanediol mono(meth)acrylate by direct esterification of (meth)acrylic acid with 1,4-butanediol in the presence of acidic esterification catalysts, with removal of the resulting water by azeotropic distillation with a suitable entraining agent, wherein excellent yields of 1,4-butanediol mono(meth) acrylate are obtained using only a small relative amount of 1,4-butanediol. The characteristic feature of this procedure is that the diester is extracted from the product mixture containing monoester, diester and unconverted 1,4-butanediol and is recycled to the esterification, the procedure according to EP-A 465 853 furthermore carrying out the esterification in the presence of considerable amounts of added preformed diester.

While German Patent 1,518,572 recommends carrying out the extraction of the diester in the presence of water in order to prevent significant amounts of monoester from entering the extracting agent at the same time, the extraction of the diester in the absence of an aqueous phase is recommended according to the process of EP-A 465 853, with the consequence that the monoester entering the extracting agent in this extraction method must be subsequently washed out from said extracting agent with water and the resulting aqueous phase must be combined with the monoester-rich extraction phase.

Consequently, both according to the procedure of German Patent 1,518,572 and according to EP-A 465 853, an aqueous solution which contains unconverted 1,4-butanediol in addition to 1,4-butanediol mono(meth)acrylate is obtained in the course of the preparation.

With regard to this aqueous phase, EP-A 465 853 recommends merely separating off the low-boiling components present therein by distillation. The disadvantage of this procedure is that it gives only a 1,4-butanediol mono(meth) acrylate which is contaminated with 1,4-butanediol and is only of little use for many applications. For example, alkanediols may adversely affect the desired molecular weight in free radical polymerizations, owing to their regulating effect, or may lead to undesirable crosslinking in reactions with diisocyanates.

German Patent 1,518,572 recommends separating off 1,4-butanediol mono(meth)acrylate from the aqueous solution by extraction with a suitable organic solvent and then removing this extracting agent by distillation. However, German Patent 1,518,572 makes no mention of the fact that 1,4-butanediol remains in the resulting aqueous solution of the desired product.

It is an object of the present invention to provide a process for the preparation of 1,4-butanediol mono(meth)acrylate by esterification of (meth)acrylic acid with 1,4-butanediol, in which simple and efficient separation of the desired product from unconverted 1,4-butanediol obtained in aqueous solution is carried out.

We have found that this object is achieved by a process for the preparation of 1,4-butanediol mono(meth)acrylate by esterification of (meth)acrylic acid with 1,4-butanediol, in which an aqueous solution of unconverted 1,4-butanediol is obtained, wherein the 1,4-butanediol present in the aqueous solution is converted into readily volatile tetrahydrofuran, preferably in the presence of a catalytic amount of an acid, and the tetrahydrofuran is separated off from the aqueous solution. Strong protic acids are preferably used.

According to Ullmanns Enzyklopädie der technischen Chemie, Vol. 12, Fungizide bis Holzwerkstoffe, Verlag Chemie, Weinheim, 4th Edition (1976), page 20 et seq., tetrahydrofuran is a saturated cyclic ether which is greatly in demand simply because of its good solvent properties. For example, tetrahydrofuran (THF) is widely used as a solvent in the coating and film industry and as a cosolvent for printing inks and adhesives. According to the abovementioned reference, the boiling point of THF is 66° C. at atmospheric pressure (1 atm).

German Patent 1,043,342 discloses that THF is obtainable by catalytic dehydration of 1,4-butanediol. The same publication also discloses that undesirable secondary reactions frequently occur and all starting materials used for the process may contain not more than 30% of water. The latter is probably due to the fact that catalytic dehydration of 1,4-butanediol to THF is reversible. Thus, German Patent 848,945 states that diols are obtained if tetrahydrogenated 5-membered cyclic ethers are heated with water and that this reaction is accelerated in the presence of acidic media. The reversibility of the abovementioned dehydration is described in Lehrbuch der organischen Chemie, C. R. Noller, Springer Verlag, Heidelberg (1960), page 653.

The advantage of the novel procedure is that THF is a useful product whose boiling point is significantly below the boiling point of 1,4-butanediol, so that it can be separated off from aqueous solution by distillation with moderate energy consumption and in a simple manner.

Suitable catalytically active acids for the novel reaction are, for example, phosphoric acid, sulfuric acid, p-toluenesulfonic acid, methanesulfonic acid and other corresponding strong protic acids. Their content is, as a rule, from 0.1 to 5, frequently from 0.5 to 2,% by weight, based on the aqueous butanediol solution.

The novel process is particularly suitable for use in the case of those aqueous solutions containing unconverted 1,4-butanediol which are obtained in the course of the esterification of (meth)acrylic acid with 1,4-butanediol for the purpose of preparing 1,4-butanediol mono(meth)acrylate under the following process conditions (particularly when the starting acid used is acrylic acid):

(Meth)acrylic acid and 1,4-butanediol in an initial molar ratio of from 1:1 to 1:3 are esterified in the presence of from 0.1 to 3% by weight, based on the acid to be esterified, of an acidic catalyst (e.g. p-toluenesulfonic acid, sulfuric acid, methanesulfonic acid and phosphoric acid) at atmospheric pressure (1 atm) at from 80° to 140° C. in a cascade comprising from 2 to 4 reaction vessels, the resulting water being removed by azeotropic distillation with an entraining agent (an aliphatic or cycloaliphatic hydrocarbon whose boiling point is from 65° to 120° C. at 1 atm, preferably cyclohexane).

The amount of the azeotropic entraining agent is advantageously such that the mixture discharged from the final vessel of the reactive cascade contains from 20 to 40% by weight of entraining agent.

The mixture discharged from the reactor is fed continuously in the middle section of an extraction column (preferably a packed column containing Raschig rings) having from 2 to 10, preferably from 4 to 6, theoretical plates. Here, the middle section of the extraction column is understood in particular to be the section which, considered from the middle of the section having the extractive effect (the total zone having an extractive effect) of the extraction column, also comprises 50% of the upper section having an extractive effect and 50% of the lower section having an extractive effect, said sections being part of the extraction column.

Water is added at the top of the extraction column while the extraction agent which has a lower specific gravity and is chosen to be chemically identical to the entraining agent chosen for the esterification is added at the lower end of the column via a pulsation pump. The extraction temperature is from 20° to 40° C. The extracting agent, the material to be extracted and the water are fed to the extraction column in amounts by weight such that the following is applicable:

weight of added water/weight of added material to be extracted=from 2 to 4, preferably from 2 to 3 and
weight of added extracting agent/weight of added material to be extracted=from 1 to 4, preferably from 2 to 3.

The organic phase to be removed continuously at the top of the extraction column contains essentially only 1,4-butanediol (meth)acrylate in dissolved form and is recycled to the esterification reaction. The distribution over the various cascade vessels is advantageously effected in accordance with the amount of water to be removed therefrom.

The aqueous phase to be removed continuously from the lower end of the extraction column contains essentially 1,4-butanediol mono(meth)acrylate and unconverted 1,4-butanediol.

By a subsequent extraction to be carried out in a manner known per se by means of methylene chloride, an ester of a $C_1$–$C_4$-alkanecarboxylic acid and a $C_1$–$C_5$-alkanediol or a single or mixed dialkyl ether of 4 to 8 carbon atoms, 1,4-butanediol mono(meth)acrylate is separated off from the aqueous phase. The extracting agent preferably used is isobutyl acetate. 1,4-Butanediol mono(meth)acrylate is obtainable in high purity by simple distillation.

The remaining aqueous solution contains, as a rule, $\leq 10\%$ by weight (based on solution) of unconverted 1,4-butanediol.

For example, this can be evaporated down to a water content of $\leq 30\%$ by weight, and the 1,4-butanediol present therein can then be converted by the procedure recommended in German Patent 1,043,342 into THF, which can be separated off by distillation in a manner known per se.

However, the conversion of the 1,4-butanediol remaining in the aqueous solution into THF can also be carried out surprisingly without prior concentration of the aqueous solution, with conversions of $\geq 90$ mol %, based on 1,4-butanediol.

Cyclization is preferably carried out under autogenous pressure at from 140° to 200° C. in the presence of from 0.1 to 5% by weight of a strong acid.

The reaction is advantageously carried out in a flow tube during residence times of from 10 to 100 minutes. The reaction is preferably effected in two reaction tubes connected in series, and some of the THF formed is separated off by stripping in an intermediate reaction kettle by letting down the pressure (preferably 1.5 atm, 110° C.). The THF formed is advantageously separated off by rectification from the mixture discharged from the second reaction tube (usually P=1 atm), the aqueous THF obtained during the intermediate stripping preferably also being added in the upper section of the column. The resulting azeotropic THF/water mixture is worked up in a manner known per se. Advantageously, the residence time in the two reaction tubes connected in series is from 15 to 25 minutes (per reaction tube).

In the procedure outlined above, (meth)acrylic acid conversions of $\geq 95$ mol % in conjunction with a 1,4-butanediol conversion of $\geq 99$ mol % is achievable in the classical esterification of (meth)acrylic acid with 1,4-butanediol for the preparation of 1,4-butanediol monoacrylate. More than 98 mol % of the 1,4-butanediol used are converted into the desired products 1,4-butanediol mono(meth)acrylate and THF. The end product 1,4-butanediol mono(meth)acrylate is obtained in a purity of $\leq 99\%$ by weight.

Of course, all process steps on the route to the monoester of (meth)acrylic acid are carried out in the presence of conventional amounts of usual polymerization inhibitors. Examples of these are phenothiazine, hydroquinone and hydroquinone monomethyl ether.

EXAMPLE

After the addition of 1% by weight (based on the solution) of concentrated sulfuric acid, a 5% strength by weight solution of 1,4-butanediol in water was passed through two reaction tubes connected in series, during a residence time of 20 min in each case and at 180° C. and 12.5 atm. After leaving the first reaction tube, the mixture was let down to 1.5 atm and 110° C., THF formed being evaporated. The mixture discharged from the reactor was then distilled together with the vapors from the intermediate let-down stage.

The resulting conversion of 1,4-butanediol to THF was ≧95 mol %.

We claim:

1. A process for the preparation of 1,4-butanediol mono (meth)acrylate by esterification of (meth)acrylic acid with 1,4-butanediol, in which an aqueous solution of unconverted 1,4-butanediol is obtained, wherein the 1,4-butanediol present in the aqueous solution is converted into tetrahydrofuran and the tetrahydrofuran is separated off from the aqueous solution.

2. A process as claimed in claim 1, wherein the 1,4-butanediol present in the aqueous solution is converted into tetrahydrofuran in the presence of a catalytic amount of an acid.

3. A process as claimed in claim 1, wherein the resulting aqueous 1,4-butanediol solution contains ≦10% by weight, based on the solution, of 1,4-butanediol.

4. A process as claimed in claim 1, wherein the conversion of the 1,4-butanediol present in the aqueous solution into tetrahydrofuran is carried out without prior concentration of said solution.

5. A process as claimed in claim 1, wherein the conversion of the 1,4-butanediol into tetrahydrofuran is carried out at from 140° to 200° C.

6. A process as claimed in claim 1, wherein the reaction is carried out in a flow tube during a residence time of from 10 to 100 minutes.

7. A process as claimed in claim 1, which is a process for the preparation of 1,4-butanediol acrylate.

* * * * *